United States Patent
Takayama

(10) Patent No.: US 9,274,234 B2
(45) Date of Patent: Mar. 1, 2016

(54) NUCLEAR MEDICINE IMAGING APPARATUS AND NUCLEAR MEDICINE IMAGING SYSTEM

(75) Inventor: Takuzo Takayama, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/459,798

(22) Filed: Apr. 30, 2012

(65) Prior Publication Data

US 2012/0215100 A1 Aug. 23, 2012

Related U.S. Application Data

(63) Continuation of application No. PCT/JP2011/067700, filed on Aug. 2, 2011.

(30) Foreign Application Priority Data

Aug. 9, 2010 (JP) ................................. 2010-178592

(51) Int. Cl.
- *A61B 5/05* (2006.01)
- *G01T 1/164* (2006.01)
- *A61B 6/03* (2006.01)

(52) U.S. Cl.
CPC ............... *G01T 1/1647* (2013.01); *A61B 6/037* (2013.01)

(58) Field of Classification Search
USPC .................... 600/431, 436; 250/363, 379, 252
See application file for complete search history.

(56) References Cited

U.S. PATENT DOCUMENTS

| | | | | |
|---|---|---|---|---|
| 6,072,177 | A | * | 6/2000 | McCroskey et al. ........ 250/252.1 |
| 2007/0090297 | A1 | * | 4/2007 | Rutten et al. ............. 250/363.03 |
| 2008/0195249 | A1 | * | 8/2008 | Rousso et al. ................ 700/231 |
| 2010/0078583 | A1 | | 4/2010 | Tsubota et al. |

FOREIGN PATENT DOCUMENTS

| | | |
|---|---|---|
| CN | 101111781 A | 1/2008 |
| JP | 5-80155 | 4/1993 |
| JP | 6-34760 | 2/1994 |

(Continued)

OTHER PUBLICATIONS

International Search Report mailed Nov. 15, 2011 in PCT/JP2011/06770 filed Aug. 2, 2011 (with English Translation).

(Continued)

*Primary Examiner* — Joel F Brutus
(74) *Attorney, Agent, or Firm* — Oblon, McClelland, Maier & Neustadt, L.L.P.

(57) ABSTRACT

A PET apparatus includes a clock unit. The clock unit includes: a time measuring unit that measures a time; and a reference time receiving unit that receives a reference time. The PET apparatus also includes a detection time revising unit. By using the reference time received by the reference time receiving unit, the detection time revising unit revises detection times recorded by using the time measured by the time measuring unit. For example, the detection time revising unit revises the detection times by calculating a time error that occurred during an image taking period of a predetermined image taking process by using the time measured by the time measuring unit and the reference time received by the reference time receiving unit and further distributing the calculated time error to each of the detection times recorded during the image taking period.

7 Claims, 10 Drawing Sheets

(56) References Cited

FOREIGN PATENT DOCUMENTS

| | | |
|---|---|---|
| JP | 2000-235093 | 8/2000 |
| JP | 2002-263074 | 9/2002 |
| JP | 2005-172561 | 6/2005 |
| JP | 2006-68389 | 3/2006 |
| JP | 2006-84432 | 3/2006 |
| JP | 2008-125530 | 6/2008 |
| JP | 2009-28426 | 2/2009 |
| JP | 2010-81960 | 4/2010 |
| JP | 2010-256176 | 11/2010 |

OTHER PUBLICATIONS

International Written Opinion mailed Nov. 15, 2011 in PCT/JP2011/067700 filed Aug. 2, 2011.

Nago Bijutsu Insatsu Kabushiki Kaisha, "Medical Image/Radiological Equipment Hand Book", Japan Industries Association of Radiological Systems, 2001, 5 pages (with Partial English Translation).

Office Action issued May 29, 2013 in Chinese Patent Application No. 201180001962.3.

* cited by examiner

| MODULE ID | SCINTILLATOR NUMBER (P) | ENERGY VALUE (E) | DETECTION TIME (T) |
|---|---|---|---|
| D1 | P11 | E11 | T11 |
|  | P12 | E12 | T12 |
|  | P13 | E13 | T13 |
|  | ⋮ | ⋮ | ⋮ |

| MODULE ID | SCINTILLATOR NUMBER (P) | ENERGY VALUE (E) | DETECTION TIME (T) |
|---|---|---|---|
| D2 | P21 | E21 | T21 |
|  | P22 | E22 | T22 |
|  | P23 | E23 | T23 |
|  | ⋮ | ⋮ | ⋮ |

| MODULE ID | SCINTILLATOR NUMBER (P) | ENERGY VALUE (E) | DETECTION TIME (T) |
|---|---|---|---|
| D3 | P31 | E31 | T31 |
|  | P32 | E32 | T32 |
|  | P33 | E33 | T33 |
|  | ⋮ | ⋮ | ⋮ |

| COUNT NUMBER | SCINTILLATOR NUMBER (P) | ENERGY VALUE (E) | DETECTION TIME (T) | SCINTILLATOR NUMBER (P) | ENERGY VALUE (E) | DETECTION TIME (T) |
|---|---|---|---|---|---|---|
| 1 | P11 | E11 | T11 | | | |
| 2 | P12 | E12 | T12 | P22 | E22 | T22 |
| 3 | P13 | E13 | T13 | P32 | E32 | T32 |
| ... | ... | ... | ... | P33 | E33 | T33 |
| | | | | ... | ... | ... |

NUCLEAR MEDICINE IMAGING APPARATUS AND NUCLEAR MEDICINE IMAGING SYSTEM

CROSS-REFERENCE TO RELATED APPLICATIONS

This application is a continuation of PCT international application Ser. No. PCT/JP2011/067700 filed on Aug. 2, 2011 which designates the United States, and which claims the benefit of priority from Japanese Patent Application No. 2010-178592, filed on Aug. 9, 2010; the entire contents of which are incorporated herein by reference.

FIELD

Exemplary embodiments relate to a nuclear medicine imaging apparatus and a nuclear medicine imaging system.

BACKGROUND

As a nuclear medicine imaging apparatus, Positron Emission computed Tomography (PET) apparatuses are conventionally known. A PET apparatus generates, for example, a function image of a tissue in a human body. More specifically, to perform an image taking process using a PET apparatus, a subject is first dosed with a radiopharmaceutical labeled with a positron emitting nuclide. After that, the positron emitting nuclide that is selectively taken into a body tissue within the subject releases positrons, and the released positrons are coupled with electrons and annihilated. At this time, the positrons release a pair of gamma rays in substantially opposite directions. The PET apparatus detects the gamma rays by using a detector arranged in a ring formation so as to surround the subject and generates simultaneous count information (hereinafter, a "coincidence list") from the detection result. Further, the PET apparatus performs a reconstructing process through a back-projection process by using the generated coincidence list and generates a PET image.

In this situation, the radiopharmaceutical refers to a pharmaceutical in which a radio isotope (RI) is used. During an image taking process using a PET apparatus, it is required to accurately understand the radioactivity level of the radiopharmaceutical with which the subject is dosed. However, because the radioactivity level of a radiopharmaceutical decays over the course of time (see FIG. 12), the radioactivity level is usually understood by using a test time indicating the time at which the radioactivity level of the radiopharmaceutical is measured and a detection time indicating a time at which gamma rays are detected by a PET apparatus. For example, a time difference is calculated between the test time measured by a radioactivity measuring apparatus and the detection time at which the gamma rays are detected by the PET apparatus, so that the radioactivity level at the time of the detection of the gamma rays can be estimated by referring to a decay curve while using the calculated time difference and the radioactivity value at the test time. FIG. 12 is a drawing for explaining the decay of the radioactivity level of a radiopharmaceutical.

However, the clock used by the radioactivity measuring apparatus to measure the test time is different from the clock used by the PET apparatus to measure the detection time. For this reason, if the clock used by the PET apparatus is not accurate, for example, it means that the detection time itself is not accurately measured. Thus, even if the time difference between the test time and the detection time is calculated, the calculated time difference is inaccurate. As a result, conventional techniques have a problem where it is not necessarily always possible to accurately understand the radioactivity level of the radiopharmaceutical with which the subject is dosed.

BRIEF DESCRIPTION OF THE DRAWINGS

FIG. 5 is a drawing of an example of a coincidence list stored in a coincidence list storage unit according to the first embodiment.

DETAILED DESCRIPTION

Figure 1:
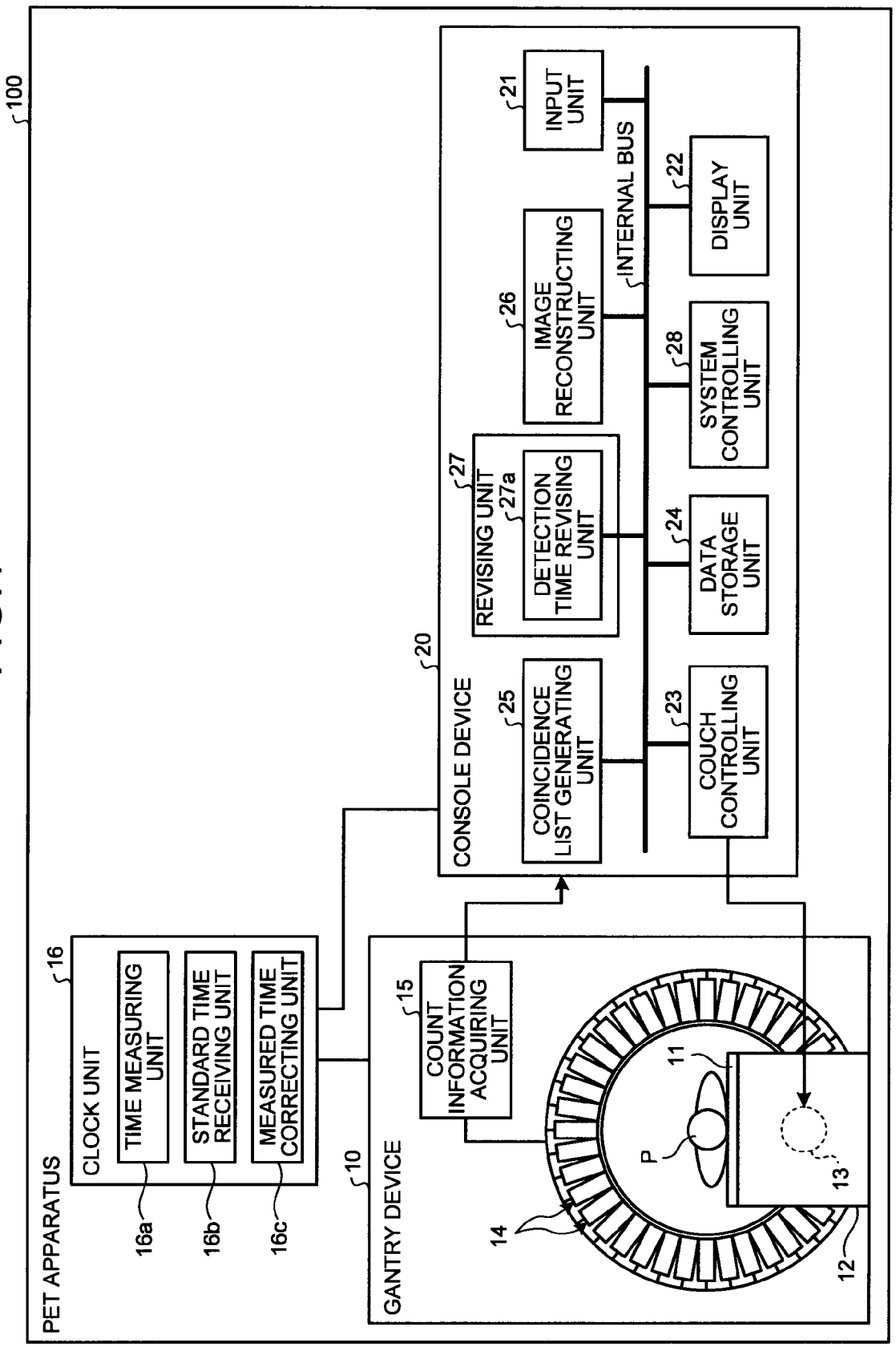
FIG. 1 is a block diagram of a PET apparatus according to a first embodiment.

A nuclear medicine imaging apparatus according to an embodiment is configured to detect radiation emitted by a nuclide with which a subject is dosed and to reconstruct a nuclear medicine image. The nuclear medicine imaging apparatus according to an embodiment includes a time measuring unit, a reference time receiving unit, a detection time recording unit, and a revising unit. The time measuring unit is configured to measure a time. The reference time receiving unit is configured to receive a reference time used as a reference for the measuring of the time. The detection time recording unit is configured to record detection times at each of which the radiation is detected, by using the time measured by the time measuring unit. The revising unit is configured to revise the detection times recorded by the detection time recording unit, by using the reference time received by the reference time receiving unit.

A nuclear medicine imaging apparatus according to an embodiment is configured to detect radiation emitted by a nuclide with which a subject is dosed and to reconstruct a nuclear medicine image. The nuclear medicine imaging apparatus according to an embodiment includes a time measuring unit, a reference time receiving unit, a correcting unit, and a detection time recording unit. The time measuring unit is configured to measure a time. The reference time receiving unit is configured to receive a reference time used as a reference for the measuring of the time. The correcting unit is configured to correct the time measured by the time measuring unit, according to the reference time received by the reference time receiving unit. The detection time recording unit is configured to record a detection time at which the radiation is detected, by using the time measured by the time measuring unit.

A nuclear medicine imaging system according to an embodiment includes a measuring apparatus and a nuclear medicine imaging apparatus. The measuring apparatus is configured to measure a radioactivity level of a nuclide with which a subject is dosed. The nuclear medicine imaging apparatus is configured to detect radiation emitted by the nuclide and to reconstruct a nuclear medicine image. The measuring apparatus includes a signal transmitting unit. The signal transmitting unit is configured to transmit a signal indicating timing corresponding to a test time at which the radioactivity level is measured, to the nuclear medicine imaging apparatus. The nuclear medicine imaging apparatus includes a signal receiving unit, a time measuring unit, and a detection time recording unit. The signal receiving unit is configured to receive the signal transmitted by the signal transmitting unit. The time measuring unit is configured to measure a time while using the timing indicated by the signal received by the signal receiving unit as a starting point. The detection time recording unit is configured to record a detection time at which the radiation is detected, by using the time measured by the time measuring unit.

In the following sections, as examples of a nuclear medicine imaging apparatus according to the exemplary embodiments, a PET apparatus 100 according to first and second embodiments will be explained.

First Embodiment

To accurately understand the radioactivity level of a radiopharmaceutical with which a subject is dosed, the PET apparatus 100 according to the first embodiment includes a configuration that accurately measures a detection time. More specifically, the PET apparatus 100 according to the first embodiment includes a configuration that first receives a reference time and corrects a "clock itself that measures the detection time" by using the received reference time. A clock unit 16 described later primarily corresponds to this configuration. Examples of the reference time include a standard time based on a standard time-and-frequency signal, a time signal broadcasted on the radio, or the like, as well as a reference time distributed by a time server to the apparatuses in the network thereof. Any of these examples is applicable to the PET apparatus 100 according to the first embodiment; however, an example using the standard time will be explained in the following sections. Further, the PET apparatus 100 according to the first embodiment includes a configuration that revises the "detection time itself" by using the received standard time. A revising unit 27 described later primarily corresponds to this configuration. Although the PET apparatus 100 according to the first embodiment includes both of these configurations, the PET apparatus 100 may include only one of these configurations.

<A Configuration of the Pet Apparatus 100 According to the First Embodiment>

A configuration of the PET apparatus 100 according to the first embodiment will be explained with reference to FIGS. 1 to 6. FIG. 1 is a block diagram of the PET apparatus 100 according to the first embodiment. As shown in FIG. 1, the PET apparatus 100 according to the first embodiment includes a gantry device 10 and a console device 20.

The gantry device 10 detects a pair of gamma rays emitted from a positron and acquires count information based on the detection result. As shown in FIG. 1, the gantry device 10 includes a couchtop 11, a couch 12, a couch driving unit 13, detector modules 14, and a count information acquiring unit 15. As shown in FIG. 1, the gantry device 10 has a hollow serving as an image-taking opening.

The couchtop 11 is a bed on which a subject P lies down and is positioned on top of the couch 12. Under the control of a couch controlling unit 23 (explained later), the couch driving unit 13 moves the couchtop 11. For example, by moving the couchtop 11, the couch driving unit 13 moves the subject P into the space inside the image-taking opening of the gantry device 10.

The detector modules 14 detect the gamma rays emitted from the subject P. As shown in FIG. 1, within the gantry device 10, the plurality of detector modules 14 are arranged in a ring formation so as to surround the subject P.

Figure 2A:
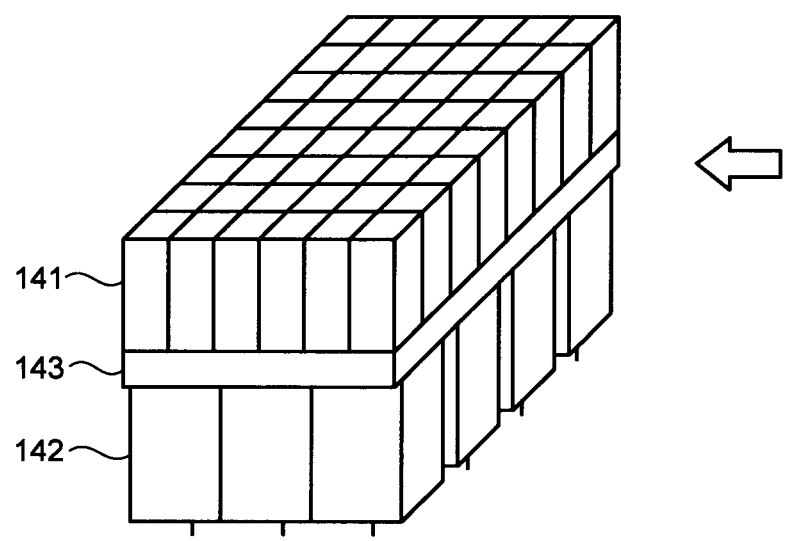
FIG. 2A is a drawing for explaining a detector module according to the first embodiment.
Figure 2B:
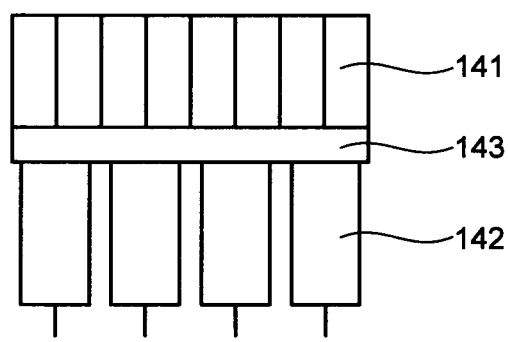
FIG. 2B is another drawing for explaining the detector module according to the first embodiment.

FIGS. 2A and 2B are drawings for explaining the detector modules 14 according to the first embodiment. As shown in FIG. 2A, each of the detector modules 14 is an Anger-type detector that uses a photon counting method. Each of the detector modules 14 includes scintillators 141, photomultiplier tubes (may be referred to as "PMTs") 142, and a light guide 143. FIG. 2B depicts the detector module 14 viewed from the direction of the arrow shown in FIG. 2A.

The scintillators 141 convert the gamma rays that are emitted from the subject P and entered therein into visible light and output the visible light (hereinafter, "scintillation light") resulting from the conversion. The scintillators 141 are configured with scintillator crystals of, for example, NaI (sodium iodide), BGO (bismuth germanate), LYSO (lutetium yttrium oxyorthosilicate), LSO (lutetium oxyorthosilicate), LGSO (lutetium gadolinium oxyorthosilicate), or the like. As shown in FIG. 2A, the scintillators 141 are arranged in a two-dimensional formation. Further, the photomultiplier tubes 142 multiply the scintillation light output from the scintillators 141 and covert the multiplied scintillation light into an electric signal. As shown in FIG. 2A, the plurality of photomultiplier tubes 142 are provided. The light guide 143 transfers the scintillation light output from the scintillator 141 to the photomultiplier tubes 142. The light guide 143 is configured by using, for example, a plastic material having an excellent light transmitting characteristic.

Each of the photomultiplier tubes 142 includes a photocathode that receives the scintillation light and generates photoelectrons; multiple stages of dynodes that create electric fields for accelerating the generated photoelectrons; and an anode from which electrons flow out. The electrons emitted from the photocathode due to the photoelectric effect are accelerated toward a dynode and collide with the surface of the dynode, so as to knock out additional electrons. When this phenomenon is repeated at the multiple stages of dynodes, the number of electrons is multiplied in the manner of an avalanche so that the number of electrons reaches as many as approximately 1 million at the anode. In this example, the gain factor of the photomultiplier tube 142 is 1 million times. To cause this multiplication utilizing the avalanche phenomenon, a voltage of 1000 volts or higher is usually applied to between the dynodes and the anode.

In this manner, the detector modules 14 detect the gamma rays emitted from the subject P, by converting the gamma rays emitted from the subject P into the scintillation light by using the scintillators 141 and further converting the converted scintillation light into the electric signal by using the photomultiplier tubes 142.

Returning to the description of FIG. 1, the count information acquiring unit 15 acquires count information based on the detection result obtained by the detector modules 14. More specifically, the count information acquiring unit 15 acquires, for each of the detector modules 14, a detection position of a gamma ray that has entered the detector module 14, an energy value of the gamma ray at the time when the gamma ray enters the detector module 14, and a detection time of the gamma ray that has entered the detector module 14. The count information acquiring unit 15 transmits the acquired count information to the console device 20.

First, the count information acquiring unit 15 performs an Anger-type position calculating process to acquire the detection positions based on the detection result obtained by the detector modules 14. More specifically, the count information acquiring unit 15 identifies some of the photomultiplier tubes 142 that converted the scintillation light having been output from the scintillators 141 into an electric signal mutually at the same time. Further, the count information acquiring unit 15 determines scintillator numbers (P) indicating the positions of the scintillators 141 which the gamma rays entered, by calculating the position of the center of gravity while using the positions of the identified photomultiplier tubes 142 and the energy values of the gamma rays corresponding to the strengths of the electric signals. If the photomultiplier tubes 142 are position-detecting-type photomultiplier tubes, the photomultiplier tubes 142 may acquire the detection positions.

Further, by calculating the integral of the strengths of the electric signals output by the photomultiplier tubes 142, the count information acquiring unit 15 determines the energy values (E) of the gamma rays that entered the detector modules 14. Also, the count information acquiring unit 15 acquires the detection times (T) at which the gamma rays were detected by the detector modules 14. For example, the count information acquiring unit 15 acquires the detection times (T) with a level of precision in the unit of $10^{-12}$ seconds (pico seconds). Each of the detection times (T) may be expressed as an absolute time or as a time period that has elapsed since the start of the image taking process, for example.

The count information acquiring unit 15 acquires, as the count information, the scintillator numbers (P), the energy values (E), and the detection times (T) in this manner.

In the present example, the PET apparatus 100 according to the first embodiment includes, as explained below, the clock unit 16. A time measuring unit 16a included in the clock unit 16 measures the time used in the PET apparatus 100. Accordingly, the detection times (T) acquired by the count information acquiring unit 15 are pieces of information based on the time measured by the time measuring unit 16a.

The clock unit 16 measures the time. As shown in FIG. 1, the clock unit 16 includes the time measuring unit 16a, a standard time receiving unit 16b, and a measured time correcting unit 16c.

The time measuring unit 16a is a clock that measures the time used in the PET apparatus 100. Further, the time measured by the time measuring unit 16a is used in processes performed by the count information acquiring unit 15. In other words, as mentioned above, the count information acquiring unit 15 acquires the detection times (T) by using the time measured by the time measuring unit 16a. Further, the detection times (T) acquired by the count information acquiring unit 15 are recorded into a coincidence list by a coincidence list generating unit 25, which is explained later.

The standard time receiving unit 16b receives a standard time by, for example, receiving a standard time-and-frequency signal or a time signal broadcasted on the radio. Further, the standard time received by the standard time receiving unit 16b is used in processes performed by the measured time correcting unit 16c and processes performed by a detection time revising unit 27a, which is explained later. In the first embodiment, the standard time receiving unit 16b may receive the standard time once a day in an example or may receive the standard time a number of times a day in another example.

The measured time correcting unit 16c corrects the time measured by the time measuring unit 16a, according to the standard time received by the standard time receiving unit 16b. The measured time correcting unit 16c according to the first embodiment corrects the time when, for example, the PET apparatus 100 is activated. Further, the measured time correcting unit 16c corrects the time, for example, in synchronization with a time at which the standard time is received by the standard time receiving unit 16b. Also, the measured time correcting unit 16c corrects the time, for example, upon receipt of an instruction from an operator when the operator particularly determines that it is necessary. A time at which the standard time is received by the standard time receiving unit 16b does not necessarily have to be in synchronization with a time at which the time is corrected by the measured time correcting unit 16c.

In this situation, the measured time correcting unit 16c according to the first embodiment avoids the situation where the time is corrected during an image taking process, by using one or both of the two methods described below. The reason is that, if the time measured by the time measuring unit 16a is corrected while the count information acquiring process or the like is being performed during an image taking process performed by the PET apparatus 100, the integrity among the detection times will be lost from a series of pieces of data acquired during the image taking process, and it will become impossible to accurately understand the radioactivity level of the radiopharmaceutical with which the subject was dosed.

For this reason, as one of the methods, before correcting the time measured by the time measuring unit 16a, the measured time correcting unit 16c according to the first embodiment displays a checking screen on a display unit 22 to check to see if a correcting process should be performed and, if the condition is satisfied where a permission to perform the correcting process is received via an input unit 21, the measured time correcting unit 16c corrects the time.

For example, before correcting the time, the measured time correcting unit 16c displays, on the display unit 22, the checking screen showing a sentence such as "Would you like to set the hands of the clock to the standard time?" as well as "OK" and "NG" buttons. Further, if the condition is satisfied where the operator of the PET apparatus 100 has pressed the "OK" button, the measured time correcting unit 16c corrects the time.

Further, as the other method, before correcting the time measured by the time measuring unit 16a, the measured time correcting unit 16c according to the first embodiment judges whether the timing with which the correcting process is to be performed affects the image taking process. If the timing is such that the image taking process is to be affected, the measured time correcting unit 16c cancels the time correcting process.

For example, before correcting the time, the measured time correcting unit 16c transmits an inquiry to a system controlling unit 28 and obtains an image taking process starting time specified in an image taking plan. Subsequently, the measured time correcting unit 16c compares the obtained image taking process starting time with the time measured by the time measuring unit 16a and judges whether an image taking process is currently being performed or an image taking process is to be started within a predetermined time period. As a result, if the measured time correcting unit 16c determines that no image taking process is currently being performed, and also, no image taking process is scheduled to be started within the predetermined time period, the measured time correcting unit 16c corrects the time.

Returning to the description of FIG. 1, the console device 20 receives an operation performed on the PET apparatus 100 by an operator, controls a PET image taking process, and reconstructs a PET image by using the count information acquired by the gantry device 10. More specifically, as shown in FIG. 1, the console device 20 includes the input unit 21, the display unit 22, the couch controlling unit 23, a data storage unit 24, the coincidence list generating unit 25, an image reconstructing unit 26, the revising unit 27, and the system controlling unit 28. The functional units included in the console device 20 are connected to one another via an internal bus.

The input unit 21 is configured with a mouse and/or a keyboard used by the operator of the PET apparatus 100 for inputting various types of instructions and various types of settings and is configured so as to transfer the input various instructions and settings to the system controlling unit 28. The display unit 22 is a monitor or the like referenced by the operator. Under the control of the system controlling unit 28, the display unit 22 displays PET images, and also, displays a Graphical User Interface (GUI) for receiving the various types of instructions and the various types of settings from the operator. The couch controlling unit 23 controls the couch driving unit 13.

Figures 3, 4:
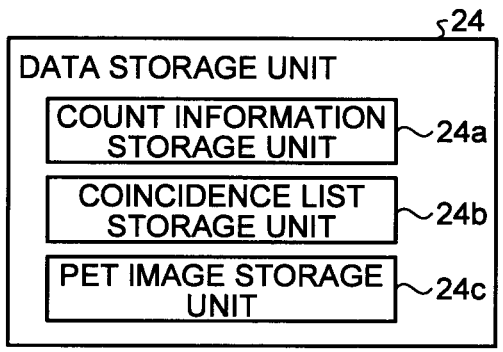
FIG. 3 is a drawing for explaining a data storage unit according to the first embodiment.
FIG. 4 is a drawing of an example of count information stored in a count information storage unit according to the first embodiment.

The data storage unit 24 stores therein various types of data used in the PET apparatus 100. FIG. 3 is a drawing for explaining the data storage unit 24 according to the first embodiment. As shown in FIG. 3, the data storage unit 24 includes a count information storage unit 24a, a coincidence list storage unit 24b, and a PET image storage unit 24c. The data storage unit 24 is realized with, for example, a semiconductor memory element such as a Random Access Memory (RAM) or a flash memory, a hard disk, or an optical disk.

The count information storage unit 24a stores therein the count information for each of the detector modules 14 acquired by the count information acquiring unit 15. More specifically, the count information storage unit 24a stores therein the count information for each of the detector modules 14 transmitted from the count information acquiring unit 15. Further, the count information stored in the count information storage unit 24a is used for processes performed by the coincidence list generating unit 25. The count information stored in the count information storage unit 24a may be deleted or may be stored for a predetermined period of time after being used for the processes performed by the coincidence list generating unit 25.

FIG. 4 is a drawing of an example of the count information stored in the count information storage unit 24a according to the first embodiment. As shown in FIG. 4, the count information storage unit 24a stores therein the scintillator numbers (P), the energy values (E), and the detection times (T), in correspondence with modules IDs each identifying a different one of the detector modules 14.

The coincidence list storage unit 24b stores therein the coincidence list generated by the coincidence list generating unit 25. More specifically, the coincidence list storage unit 24b stores the coincidence list therein, as a result of the coincidence list generating unit 25 storing the coincidence list into the coincidence list storage unit 24b. Further, the coincidence list stored in the coincidence list storage unit 24b is used for processes performed by the image reconstructing unit 26. The coincidence list stored in the coincidence list storage unit 24b may be deleted or may be stored for a predetermined period of time after being used for the processes performed by the image reconstructing unit 26.

FIG. 5 is a drawing of an example of the coincidence list stored in the coincidence list storage unit 24b according to the first embodiment. As shown in FIG. 5, the coincidence list storage unit 24b stores therein sets of count information in correspondence with count numbers that indicate the order in which the items in the coincidence list have been generated in a time sequence.

The PET image storage unit 24c stores therein the PET image reconstructed by the image reconstructing unit 26. More specifically, the PET image storage unit 24c stores the PET image therein as a result of the image reconstructing unit 26 storing the PET image into the PET image storage unit 24c. Further, the PET image stored in the PET image storage unit 24c is displayed on the display unit 22 by the system controlling unit 28.

Returning to the description of FIG. 1, the coincidence list generating unit 25 generates the coincidence list by using the count information acquired by the count information acquiring unit 15. More specifically, the coincidence list generating unit 25 reads the count information stored in the count information storage unit 24a and searches for a set of pieces of count information representing a pair of gamma rays emitted from a positron that are counted at the same time, based on the energy values and the detection times. Further, the coincidence list generating unit 25 generates the set of pieces of count information found in the search into the coincidence list and stores the generated coincidence list into the coincidence list storage unit 24b.

For example, the coincidence list generating unit 25 generates the coincidence list based on a coincidence list generating condition input by the operator. In the coincidence list generating condition, an energy window range and a time window range are specified. For example, the coincidence list generating unit 25 generates the coincidence list, based on an energy window range of "350-550 keV" and a time window range of "600 pico seconds".

For example, the coincidence list generating unit 25 refers to the energy values (E) and the detection times (T) shown in FIG. 4, by referring to the count information storage unit 24a. Further, the coincidence list generating unit 25 searches for a set of pieces of count information of which the difference in the detection times (T) is within the time window range of "600 pico seconds", and also, of which the energy values (E) are both within the energy window range of "350-550 keV", from among the detector modules 14. Further, when the coincidence list generating unit 25 finds in the search a set "P11, E11, T11" and another set "P22, E22, T22" as the sets satisfying the coincidence list generating condition, the coincidence list generating unit 25 generates these sets into the coincidence list and stores the generated coincidence list into the coincidence list storage unit 24b, as shown in FIG. 5.

The image reconstructing unit 26 reconstructs the PET image. More specifically, the image reconstructing unit 26 reconstructs the PET image by reading the coincidence list stored in the coincidence list storage unit 24b as projection data (sinogram data) and performing a back-projection process on the read projection data. Further, the image reconstructing unit 26 stores the reconstructed PET image into the PET image storage unit 24c.

The revising unit 27 revises various types of times measured in the PET apparatus 100. The revising unit 27 according to the first embodiment includes, as shown in FIG. 1, the detection time revising unit 27a. The detection time revising unit 27a revises the detection times recorded in the coincidence list by the coincidence list generating unit 25, by using the standard time received by the standard time receiving unit 16*b*.

In other words, as explained above, the detection times acquired by the count information acquiring unit 15 according to the first embodiment are pieces of information based on the time measured by the time measuring unit 16*a* and are recorded into the coincidence list by the coincidence list generating unit 25. Accordingly, the detection times recorded into the coincidence list by the coincidence list generating unit 25 are also pieces of information based on the time measured by the time measuring unit 16*a* and are not necessarily accurate.

However, as explained above, the PET apparatus 100 according to the first embodiment is configured so that the time measured by the time measuring unit 16*a* is corrected by the measured time correcting unit 16*c*, as necessary. For this reason, it is assumed that the time measured by the time measuring unit 16*a* is also accurate in many situations; however, for example, if the operator did not give a permission to correct the time or if the time was not corrected because the image taking process was being performed, it is desirable to revise the detection times in an ex-post manner.

In this situation, the detection time revising unit 27*a* according to the first embodiment revises the detection times by using one or both of the two methods described below. As one of the methods, the detection time revising unit 27*a* according to the first embodiment receives the standard time at a predetermined time (e.g., at the start or at the end of an image taking process) during a predetermined image taking process and revises the detection times in an ex-post manner by using a time error obtained at the predetermined time.

For example, the detection time revising unit 27*a* obtains the image taking process starting time specified in the image taking plan from the system controlling unit 28 and instructs the standard time receiving unit 16*b* to receive the standard time, when the time measured by the time measuring unit 16*a* becomes equal to the image taking process starting time. Subsequently, the detection time revising unit 27*a* calculates the time error between the time measured by the time measuring unit 16*a* and the standard time received by the standard time receiving unit 16*b*. Further, the detection time revising unit 27*a* reflects the calculated time error on the detection times in the coincidence list generated by the coincidence list generating unit 25 in an ex-post manner.

For example, if the time error is "−3 minutes (3 minutes slower than the standard time)", the detection time revising unit 27*a* uniformly advances the detection times in the coincidence list by three minutes. On the assumption that the clock used by the radioactivity measuring apparatus to measure the test time is accurate (i.e., the clock matches the standard time), although there was a three-minute gap before the revising process, the gap is eliminated after the revising process. Thus, it is possible to accurately understand the radioactivity level of the radiopharmaceutical with which the subject was dosed.

As the other method, the detection time revising unit 27*a* according to the first embodiment measures times before and after the predetermined image taking process so as to revise the detection times in an ex-post manner by using a time error that occurred during the image taking period. This revising process is particularly effective in, for example, a dynamic image-taking process or the like in which pieces of data are acquired at regular intervals of a predetermined time length so that PET images are generated at the regular intervals of the predetermined time length.

Figure 6:
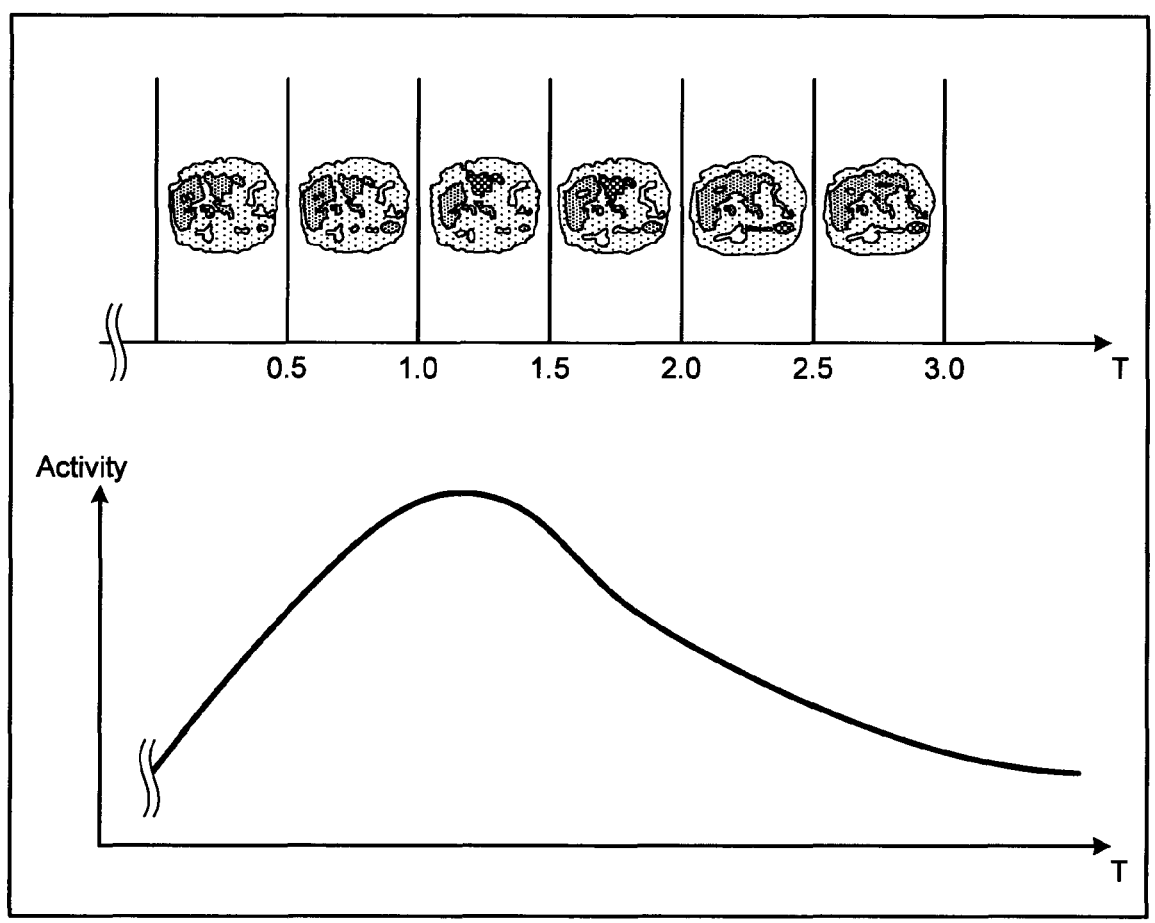
FIG. 6 is a chart for explaining a relationship between a dynamic image-taking process and a time-activity curve.

FIG. 6 is a chart for explaining a relationship between a dynamic image-taking process and a time-activity curve. As shown in FIG. 6, during a dynamic image-taking process, the PET apparatus 100 acquires pieces of data at regular intervals (e.g., once in 0.5 second), so as to reconstruct PET images having intervals of, for example, 0.5 second. As shown in FIG. 6, during a dynamic image-taking process, it is important to obtain a time-activity curve with a high level of precision, and also, it is important to accurately calculate the correspondence relationship between the time and the values of radioactivity.

Incidentally, if an image taking process takes a long time (e.g., one hour), there is a possibility that a time error may occur during the image taking period. In other words, there is a possibility that the time error at the image taking process starting time may be different from the time error at the image taking process ending time. In this situation, the method described above by which the detection times in the coincidence list are uniformly revised does not necessarily achieve an accurate revision.

For example, in a situation where the time error at an image taking process starting time is "−3 minutes (3 minutes slower than the standard time)", whereas the time error at an image taking process ending time is "−8 minutes (8 minutes slower than the standard time)", the detection time at the start of the image taking process should be revised by being advanced by three minutes, while the detection time at the end of the image taking process should be advanced by eight minutes, to perform the revising process properly. In other words, if an image taking process takes a long time so that there is a possibility that the deviation from the standard time may gradually become larger during the image taking period, it is desirable to also revise the revision of the detection times as much as possible, in accordance with the slope of the deviation.

For example, the detection time revising unit 27*a* obtains the image taking process starting time and the image taking process ending time specified in the image taking plan from the system controlling unit 28 and instructs the standard time receiving unit 16*b* to receive the standard time when the time measured by the time measuring unit 16*a* becomes equal to the image taking process starting time and to the image taking process ending time. Subsequently, the detection time revising unit 27*a* calculates a time error between each of the times measured by the time measuring unit 16*a* and a corresponding one of the standard times received by the standard time receiving unit 16*b*. Further, by calculating the difference between the calculated time errors, the detection time revising unit 27*a* calculates a time error that occurred during the image taking period, so as to reflect the calculated time error by distributing the calculated time error to the detection times in the coincidence list generated by the coincidence list generating unit 25.

For example, in the situation where the time error at the image taking process starting time is "−3 minutes (3 minutes slower than the standard time)", whereas the time error at the image taking process ending time is "−8 minutes (8 minutes slower than the standard time)", the detection time revising unit 27*a* calculates that the time error that occurred during the image taking period is "−5 minutes". After that, the detection time revising unit 27*a* revises the detection times within the coincidence list stored in the coincidence list storage unit 24*b* in the time sequence, on the assumption that the time length increases with equal intervals, so that the revision "to advance the time by three minutes" gradually becomes close to the revision "to advance the time by eight minutes" in the time sequence.

On the premise that the measured time correcting unit 16c performs the correcting process, for example, at the start of an image taking process, the time error between the time measured by the time measuring unit 16a and the standard time received by the standard time receiving unit 16b is "0 minutes" at the start of the image taking process. In that situation, the detection time revising unit 27a is able to calculate the time error that occurred during the image taking period, only by calculating the time error between the time measured by the time measuring unit 16a and the standard time received by the standard time receiving unit 16b, at the end of the image taking process. Further, the detection time revising unit 27a reflects the calculated time error by distributing the calculated time error to the detection times in the coincidence list generated by the coincidence list generating unit 25.

Returning to the description of FIG. 1, the system controlling unit 28 exercises overall control of the PET apparatus 100 by controlling the gantry device 10 and the console device 20. For example, the system controlling unit 28 controls image taking processes performed by the PET apparatus 100.

The functional units such as the coincidence list generating unit 25, the image reconstructing unit 26, the revising unit 27, and the system controlling unit 28 are configured by using an integrated circuit such as an Application Specific Integrated Circuit (ASIC) or a Field Programmable Gate Array (FPGA) or an electronic circuit such as a Central Processing Unit (CPU) or a Micro Processing Unit (MPU).

<A Processing Procedure Performed by the Pet Apparatus 100 According to the First Embodiment>

Figure 7:
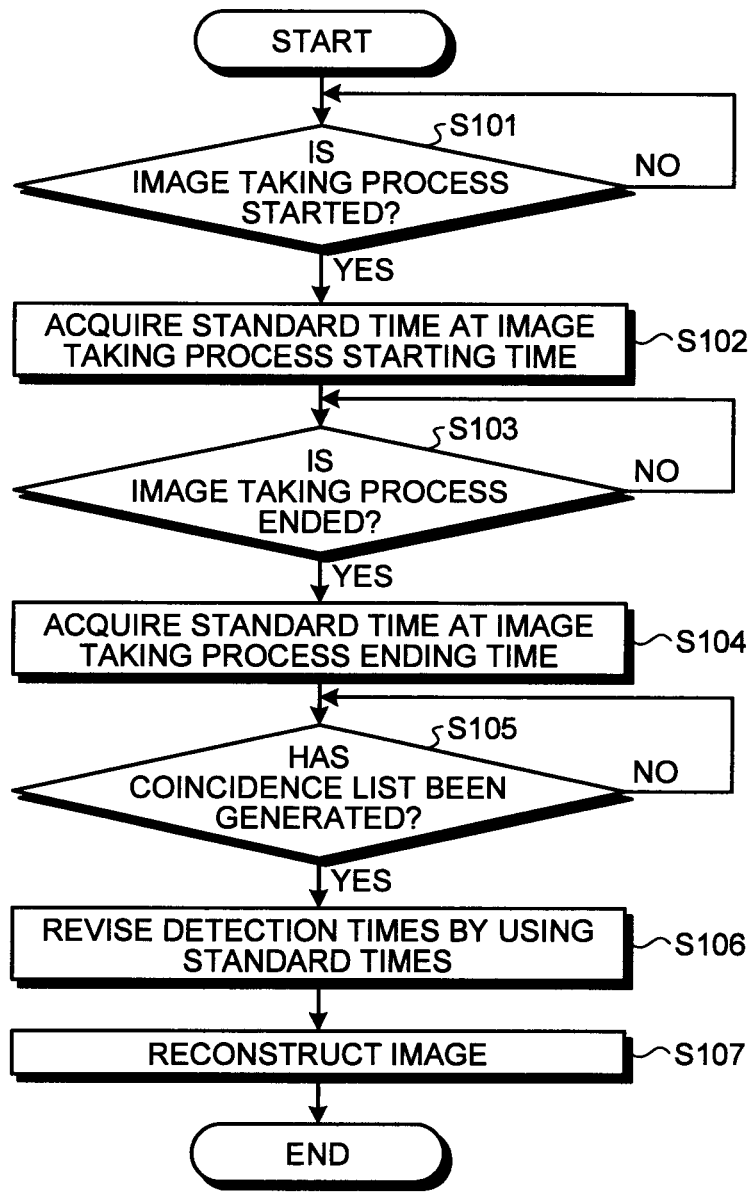
FIG. 7 is a flowchart of a processing procedure in a detection time revising process according to the first embodiment.

Next, as a processing procedure performed by the PET apparatus 100 according to the first embodiment, a processing procedure in a detection time revising process, in particular, will be explained. FIG. 7 is a flowchart of the processing procedure in the detection time revising process according to the first embodiment.

As shown in FIG. 7, in the PET apparatus 100 according to the first embodiment, the detection time revising unit 27a judges whether an image taking process is started (step S101). If the detection time revising unit 27a determines that an image taking process is started (step S101: Yes), the detection time revising unit 27a instructs the standard time receiving unit 16b to receive the standard time (step S102).

Subsequently, the detection time revising unit 27a judges whether the image taking process is ended (step S103). If the detection time revising unit 27a determines that the image taking process is ended (step S103: Yes), the detection time revising unit 27a instructs the standard time receiving unit 16b to receive the standard time (step S104).

Further, the detection time revising unit 27a judges whether the coincidence list generating process performed by the coincidence list generating unit 25 has finished (step S105). If the detection time revising unit 27a determines that the coincidence list generating process has finished (step S105: Yes), the detection time revising unit 27a revises the detection times by using the standard times acquired at steps S102 and S104 (step S106).

After that, the image reconstructing unit 26 reconstructs an image by using the coincidence list in which the detection times have been revised by the detection time revising unit 27a (step S107), and the series of processes has thus been completed.

Advantageous Effects of the First Embodiment

As explained above, the PET apparatus 100 according to the first embodiment is configured so that the clock unit 16 includes the time measuring unit 16a that measures the time and the standard time receiving unit 16b that receives the standard time. Further, the detection times recorded in the PET apparatus 100 are pieces of information that are based on the time measured by the time measuring unit 16a. Further, the PET apparatus 100 is configured so that the detection time revising unit 27a revises the detection times by using the standard time received by the standard time receiving unit 16b.

With these arrangements, according to the first embodiment, the detection times are revised by using the standard time. Thus, the detection times become accurate ones, so that it is possible to accurately understand the radioactivity level of the radiopharmaceutical with which the subject was dosed. Even if the radiopharmaceutical has a short half-life, it is also possible to accurately understand the radioactivity level thereof.

Further, the detection time revising unit 27a according to the first embodiment revises the detection times by calculating the time error that occurred during the image taking period of the predetermined image taking process and distributing the calculated time error to each of the detection times recorded during the image taking period.

With this arrangement, according to the first embodiment, even in the situation where there is a possibility that a time error may occur during the image taking period when, for example, the image taking process takes a long time, it is possible to accurately understand the radioactivity level of the radiopharmaceutical with which the subject was dosed. For example, this arrangement is particularly effective in a dynamic image-taking process or the like.

Further, the PET apparatus 100 according to the first embodiment is configured so that the clock unit 16 includes the measured time correcting unit 16c. The measured time correcting unit 16c corrects the time measured by the time measuring unit 16a according to the standard time received by the standard time receiving unit 16b. For example, the measured time correcting unit 16c corrects the time at a predetermined interval. Further, for example, the measured time correcting unit 16c corrects the time when the PET apparatus 100 is activated. As explained above, according to the first embodiment, the time measured by the time measuring unit 16a is automatically corrected.

Further, for example, before correcting the time, the measured time correcting unit 16c displays the checking screen on the display unit 22 to check to see whether the time should be corrected and, if the condition is satisfied where a permission to correct the time has been received, the measured time correcting unit 16c corrects the time. Further, as another example, before correcting the time, the measured time correcting unit 16c judges whether the timing with which the time correcting process is to be performed affects the image taking process and, if the timing is such that the image taking process is to be affected, the measured time correcting unit 16c cancels the correcting process. With these arrangements, according to the first embodiment, it is also possible to avoid the situation where the time is corrected during the image taking process.

Second Embodiment

Next, a PET system according to the second embodiment will be explained. The PET system according to the second embodiment includes, in addition to the PET apparatus 100, a radiopharmaceutical producing apparatus 250 that produces a radiopharmaceutical and a radiopharmaceutical radioactivity measuring apparatus 200 (hereinafter, the "radioactivity measuring apparatus 200"). An object of the first embodiment is to accurately calculate the time difference between the test time and the detection time by accurately measuring the detection time at least in the PET apparatus 100. In contrast, an object of the second embodiment is to accurately measure the test time, also in the radioactivity measuring apparatus 200. Thus, the time difference between the test time and the detection time becomes even more accurate.

Figure 8:
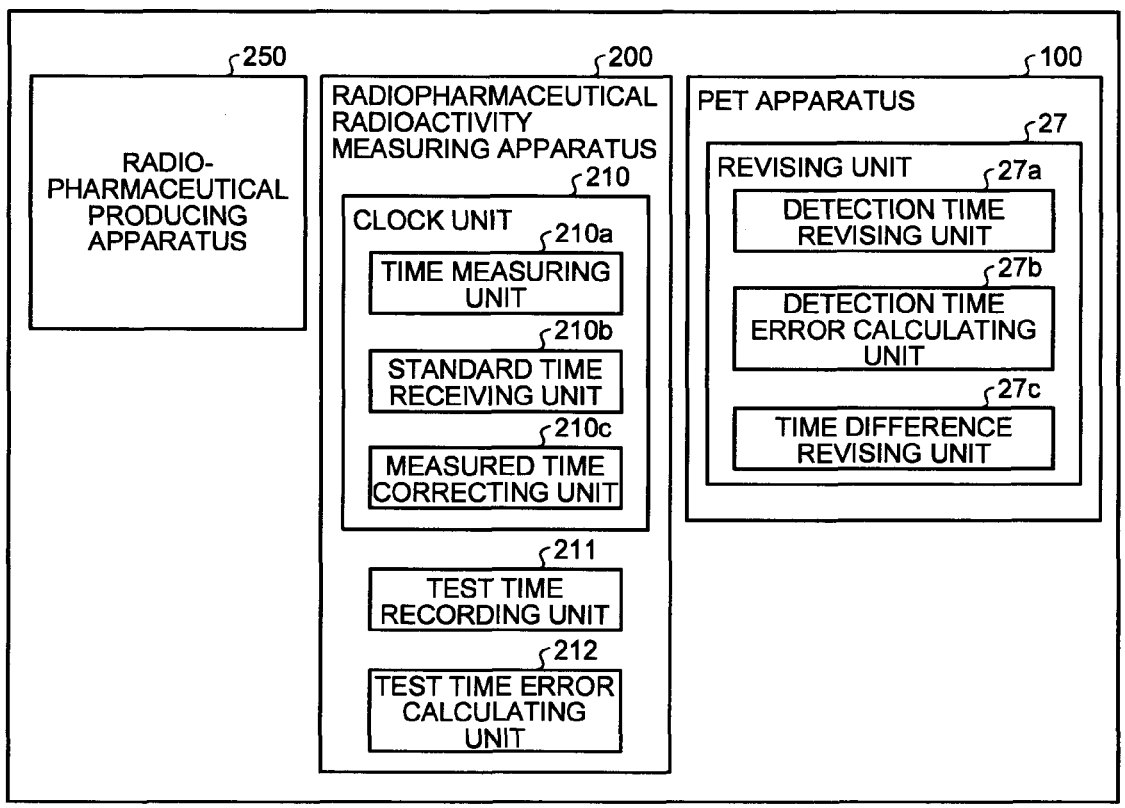
FIG. 8 is a block diagram of a PET system according to a second embodiment.

FIG. 8 is a block diagram of the PET system according to the second embodiment. The radiopharmaceutical producing apparatus 250 is an apparatus that produces a pharmaceutical labeled with a positron emitting nuclide. The radioactivity measuring apparatus 200 is an apparatus that measures a level of radioactivity of the radiopharmaceutical produced by the radiopharmaceutical producing apparatus 250. The radioactivity measuring apparatus 200 measures, for example, the level of radioactivity expressed as "X millicuries" at a test time expressed as "hh:mm:ss" (hour, minute, second).

The radioactivity measuring apparatus 200 according to the second embodiment includes a configuration that first receives a reference time and corrects the "clock itself that measures a test time" by using the received reference time. A clock unit 210 described later primarily corresponds to this configuration. Examples of the reference time include a standard time based on a standard time-and-frequency signal, a time signal broadcasted on the radio, or the like, as well as a reference time distributed by a time server to the apparatuses in the network thereof. Any of these examples is applicable to the radioactivity measuring apparatus 200 according to the second embodiment; however, an example using the standard time will be explained in the following sections. Further, the radioactivity measuring apparatus 200 according to the second embodiment includes a configuration that calculates a "time error between the test time and the standard time" by using the received standard time. A test time error calculating unit 212 described later primarily corresponds to this configuration. Although the radioactivity measuring apparatus 200 according to the second embodiment includes both of these configurations, the radioactivity measuring apparatus 200 may include only one of these configurations.

As shown in FIG. 8, the radioactivity measuring apparatus 200 according to the second embodiment includes, in particular, the clock unit 210, a test time recording unit 211, and the test time error calculating unit 212. Further, the clock unit 210 includes a time measuring unit 210a, a standard time receiving unit 210b, and a measured time correcting unit 210c.

The time measuring unit 210a is a clock that measures the time used in the radioactivity measuring apparatus 200. Further, the time measured by the time measuring unit 210a is used in processes performed by the test time recording unit 211.

The standard time receiving unit 210b receives the standard time by, for example, receiving a standard time-and-frequency signal or a time signal broadcasted on the radio. Further, the standard time received by the standard time receiving unit 210b is used in processes performed by the measured time correcting unit 210c and processes performed by the test time error calculating unit 212, which is explained later. In the second embodiment, the standard time receiving unit 210b may receive the standard time once a day in an example or may receive the standard time a number of times a day in another example.

The measured time correcting unit 210c corrects the time measured by the time measuring unit 210a, according to the standard time received by the standard time receiving unit 210b. The measured time correcting unit 210c according to the second embodiment corrects the time when, for example, the radioactivity measuring apparatus 200 is activated. Further, the measured time correcting unit 210c corrects the time, for example, in synchronization with a time at which the standard time is received by the standard time receiving unit 210b. A time at which the standard time is received by the standard time receiving unit 210b does not necessarily have to be in synchronization with a time at which the time is corrected by the measured time correcting unit 210c.

The test time recording unit 211 records the test time by using the time measured by the time measuring unit 210a. The test time error calculating unit 212 calculates a time error between the test time recorded by the test time recording unit 211 and the standard time received by the standard time receiving unit 210b. For example, the test time error calculating unit 212 instructs the standard time receiving unit 210b to receive the standard time, when the test time recording unit 211 records the test time. Further, the test time error calculating unit 212 calculates the time error between the test time recorded by the test time recording unit 211 and the standard time received by the standard time receiving unit 210b and outputs the calculated time error, together with the test time.

The PET apparatus 100 is configured so that, in addition to the same configuration as in that of the first embodiment, the revising unit 27 includes a detection time error calculating unit 27b and a time difference revising unit 27c, as shown in FIG. 8. As explained above, the radioactivity measuring apparatus 200 according to the second embodiment also outputs the time error together with the test time. Accordingly, the PET apparatus 100 according to the second embodiment calculates the time difference between the test time and the detection time more accurately, by also using the information of the time error output from the radioactivity measuring apparatus 200.

More specifically, the detection time error calculating unit 27b calculates the time error between each of the detection times recorded in the coincidence list and the standard time received by the standard time receiving unit 16b. For example, at a time when an image taking process is started, the detection time error calculating unit 27b instructs the standard time receiving unit 16b to receive the standard time. Further, the detection time error calculating unit 27b calculates the time error between each of the detection times and the standard time received by the standard time receiving unit 16b.

The time difference revising unit 27c revises the time difference between the test time and the detection time, by using the time error calculated by the detection time error calculating unit 27b as well as the test time and the time error output from the radioactivity measuring apparatus 200.

Figure 9:
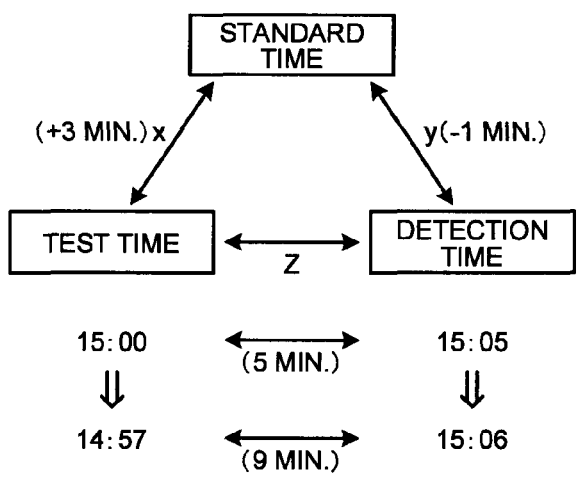
FIG. 9 is a drawing for explaining a time difference revising process.

FIG. 9 is a drawing for explaining a time difference revising process. For example, let us assume that, as shown in FIG. 9, the time error between the standard time and the test time is x minutes (e.g., +3 minutes, i.e., 3 minutes faster than the standard time). Also, let us assume that the time error between the standard time and the detection time is y minutes (e.g., −1 minute, i.e., 1 minute slower than the standard time). Further, let us assume that the time recorded as a test time was "15:00", whereas the time recorded as a detection time was "15:05".

In this situation, the time difference (z minutes) between the test time and the detection time is calculated as "5 minutes"; however, in the second embodiment, the time difference will be revised by using the time error between the standard time and the test time and the time error between the standard time and the detection time, so as to obtain an accurate time difference.

For example, the test time is revised to "14:57" by using the time error (x minutes) between the standard time and the test time. In contrast, the detection time is revised to "15:06" by using the time error (y minutes) between the standard time and the detection time. Accordingly, the time difference (z minutes) between the test time and the detection time is calculated as "9 minutes", which is an accurate time difference.

Further, for example, the sum of the time error (x minutes) between the standard time and the test time and the time error (y minutes) between the standard time and the detection time is "4 minutes". Accordingly, when "4 minutes" is added to the time difference "5 minutes" between the test time "15:00" and the detection time "15:05", the sum is "9 minutes", which is an accurate time difference.

As explained above, when the time error between the standard time and the test time as well as the time error between the standard time and the detection time are obtained, the PET apparatus 100 is able to calculate the time difference between the test time and the detection time more accurately.

The radioactivity measuring apparatus 200 according to the second embodiment is configured so that the time measured by the time measuring unit 210a is corrected by the measured time correcting unit 210c, as necessary. For this reason, it is assumed that the time measured by the time measuring unit 210a is also accurate in many situations; however, if the time was not corrected for some reason, for example, it is desirable to revise the test time in an ex-post manner. It is also possible to revise the test time by using the same method as the one used by the PET apparatus 100 according to the first embodiment to revise the detection times. Further, as explained above, the time error may be calculated together with the test time, so as to be output to the PET apparatus 100. Further, the radioactivity measuring apparatus 200 and the PET apparatus 100 may be connected to each other online, so that information is transmitted and received therebetween. Alternatively, the test time, the time error, and the like may be communicated off line.

Third Embodiment

Next, a PET system according to a third embodiment will be explained. The PET system according to the third embodiment includes a PET apparatus 300 and a radiopharmaceutical radioactivity measuring apparatus 400 (hereinafter, the "radioactivity measuring apparatus 400"). In the first and the second embodiments, the method for accurately measuring the detection time by using the reference time and the method for revising the detection time by using the reference time are explained. However, the methods for accurately calculating the time difference between the test time and the detection time are not limited to these examples. In the PET system according to the third embodiment, it is possible to accurately calculate the time difference between the test time and the detection time on the PET apparatus 300 side, by using a method by which the PET apparatus 300 is informed of "timing corresponding to the test time", that is, the timing corresponding to a "radioactivity measured value" of which the PET apparatus 300 is notified by the radioactivity measuring apparatus 400.

Figure 10:
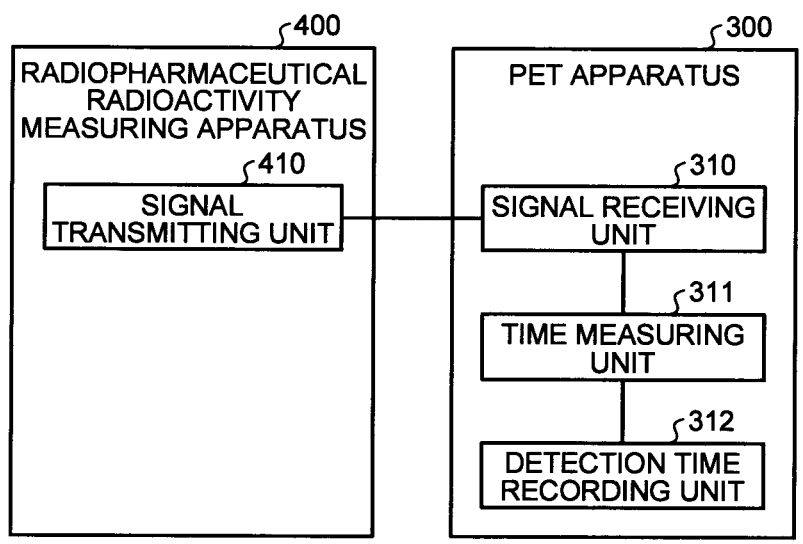
FIG. 10 is a block diagram of a PET system according to a third embodiment.

FIG. 10 is a block diagram of the PET system according to the third embodiment. The radioactivity measuring apparatus 400 includes a signal transmitting unit 410. Further, the PET apparatus 300 includes a signal receiving unit 310, a time measuring unit 311, and a detection time recording unit 312. Although each of the apparatuses includes other necessary constituent elements in addition to the constituent elements shown in FIG. 10, those are omitted from FIG. 10. For example, the PET apparatus 300 includes the gantry device 10 and the console device 20, like the PET apparatus 100 according to the first embodiment. However, the PET apparatus 300 according to the third embodiment does not necessarily have to include, for example, the clock unit 16 and/or the revising unit 27.

The signal transmitting unit 410 transmits a signal (hereinafter, the "timing signal") indicating the timing corresponding to a test time at which a radioactivity level is measured, to the PET apparatus 300. Further, the signal receiving unit 310 receives the timing signal transmitted by the signal transmitting unit 410. Further, the time measuring unit 311 measures a time, while using the timing indicated by the timing signal received by the signal receiving unit 310 as a starting point. Also, the detection time recording unit 312 records a detection time at which radiation is detected, by using the time measured by the time measuring unit 311.

Figure 11:
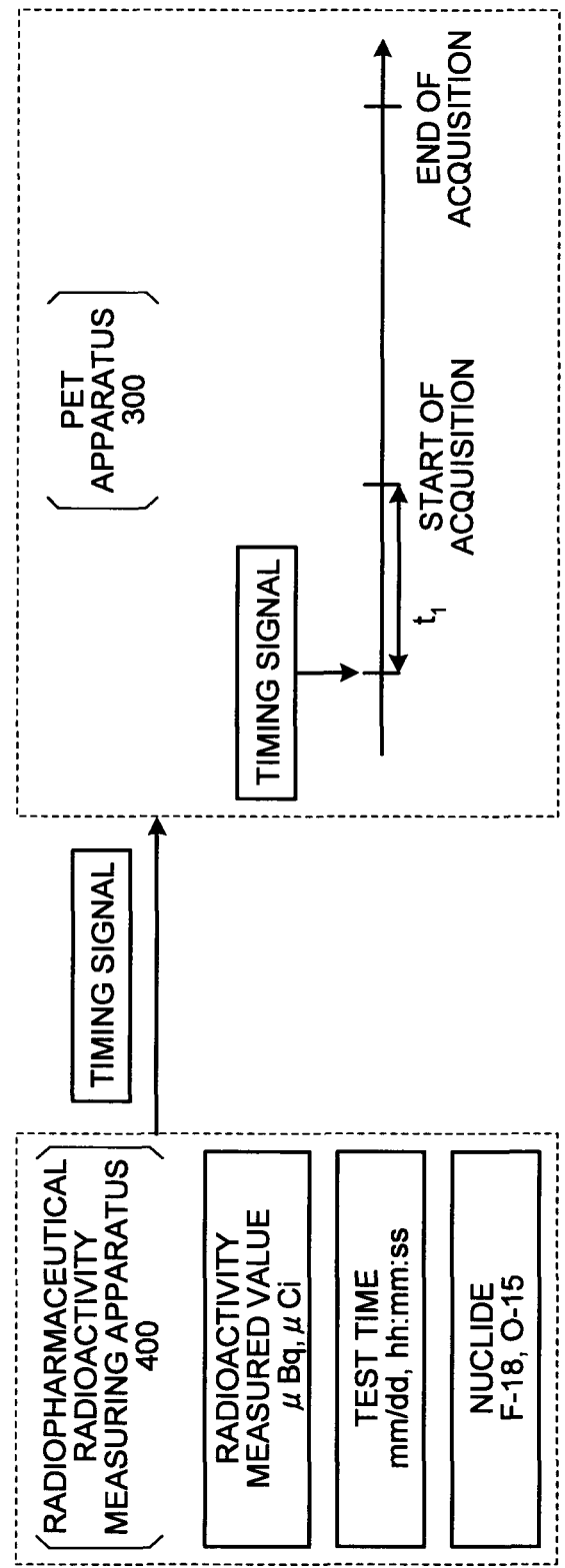
FIG. 11 is a drawing for explaining a transmission and a reception of a timing signal according to the third embodiment.
Figure 12:
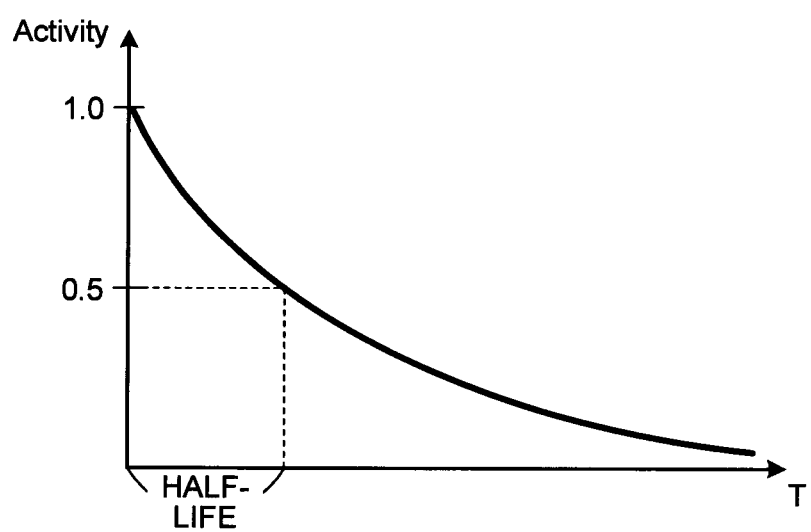
FIG. 12 is a drawing for explaining a decay of the radioactivity level of a radiopharmaceutical.

FIG. 11 is a drawing for explaining a transmission and a reception of the timing signal according to the third embodiment. First, the radioactivity measuring apparatus 400 measures a radioactivity level of the nuclide with which the subject is dosed and acquires, for example, information regarding a radioactivity measured value, a test time, and the nuclide, as shown in FIG. 11. The radioactivity measured value is the value of the measured radioactivity and is expressed by, for example, using a unit such as $\mu$Bq (microbecquerels) or $\mu$Ci (microcuries). The test time is the time at which the radioactivity measured value was measured by the radioactivity measuring apparatus 400 and is expressed by using, for example, the format "mm(month)/dd(day), hh(hour):mm(minute):ss (second)". The nuclide denotes the nuclide with which the subject is dosed and may be, for example, "F-18" or "O-15". Normally, the radioactivity measuring apparatus 400 transfers these pieces of information to the PET apparatus 300 side, as information regarding the radiopharmaceutical with which the subject is dosed. For example, these pieces of information may be transmitted to the PET apparatus 300 side, together with the timing signal. However, these pieces of information do not necessarily have to be transmitted to the PET apparatus 300 side by communication. These pieces of information may be given to an operator who operates the PET apparatus 300 by using a means other than communication (e.g., given as information written on a sheet of paper). In that situation, the operator may, for example, use necessary parts of the provided pieces of information.

In this situation, in the PET system according to the third embodiment, the signal transmitting unit 410 included in the radioactivity measuring apparatus 400 transmits the timing signal to the PET apparatus 300. As explained above, the timing signal is the signal indicating the timing corresponding to the test time at which the radioactivity level is measured. Strictly speaking, the time at which the radioactivity level is measured may be different from the test time. For example, if it takes one hour to measure the radioactivity level, the radioactivity level may be measured one hour later than the transmission of the timing signal. In that situation, for example, the radioactivity measured value at the point in time when the timing signal is transmitted is estimated by using a known decay curve, so that the PET apparatus 300 side is notified of the estimated measured value.

As shown in FIG. 11, the time measuring unit 311 included in the PET apparatus 300 measures the time, while using the timing indicated by the timing signal received by the signal receiving unit 310 as a starting point. For example, the time measuring unit 311 starts measuring the time when being triggered by the reception of the timing signal. After that, during the time period from the start of the acquisition (the image taking process) to the end of the acquisition (the image taking process), the detection time recording unit 312 records the detection time at which the radiation is detected, by using the time measured by the time measuring unit 311. With this arrangement, the detection time recorded by the detection time recording unit 312 is a time measured based on the time measuring process that is started when being triggered by the test time. Thus, the time difference between the detection time and the test time (e.g., the time that has elapsed from the test time to the detection time) is accurately measured. In this situation, the time measuring function on the radioactivity measuring apparatus 400 side and the time measuring function on the PET apparatus 300 side may work completely independently of each other.

For example, let us assume that the time period that has elapsed since the timing signal is received by the PET apparatus 300 (the test time) until the start of the acquisition is "$t_1$ seconds". In this situation, a radioactivity measured value $x_1$ obtained $t_1$ seconds later can be calculated by using Expression (1) below. In Expression (1), $x_0$ denotes the radioactivity measured value at the test time, whereas T denotes the half-life.

$$x_1 = \left(\frac{1}{2}\right)^{\frac{t_1}{T}} \times x_0 \quad (1)$$

The PET system according to the third embodiment may be used together with any of the methods explained in the first and the second embodiments. For example, in the first embodiment, the method for revising the detection time in an ex-post manner by using the received reference time is explained. This method may be applied to the third embodiment in the same manner. For example, if the image taking process takes a long time, there is a possibility that a time error may occur during the image taking period. In that situation, it is not possible to revise the time error occurring during the image taking period by only receiving the timing signal on the PET apparatus 300 side. Thus, it will be effective to use, in combination, the method by which the detection time is revised in an ex-post manner.

The PET system according to the third embodiment is explained as a system including the PET apparatus 300 and the radioactivity measuring apparatus 400. However, in addition to these apparatuses, the PET system may also include a radiopharmaceutical producing apparatus that produces a radiopharmaceutical. Further, the radiopharmaceutical producing apparatus and the radioactivity measuring apparatus 400 may be physically realized as being contained in one casing. The same applies also to the other embodiments.

Fourth Embodiment

The features disclosed herein may be implemented in various modes other than the exemplary embodiments described above.

First, in the exemplary embodiments described above, although the exemplary configuration of the PET apparatus 100 is shown in FIG. 1, the features disclosed herein are not limited to this example. For instance, the count information acquiring unit 15 may be provided on the console device 20 side. On the contrary, the coincidence list generating unit 25 may be provided on the gantry device 10 side. Further, the various types of data stored in the data storage unit 24 may be provided on the gantry device 10 side or may be provided on the console device 20 side. The time period during which each of the pieces of data is stored in the PET apparatus 100 can also be arbitrarily determined.

Further, although the exemplary embodiments are explained above while using the PET apparatus as an example, the features disclosed herein are not limited to this example. For example, the features disclosed herein are similarly applicable to any apparatus that involves recording of detection times, such as a PET-CT (Computed Tomography) apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine imaging apparatus configured to detect radiation emitted by a nuclide with which a subject is dosed and to reconstruct a nuclear medicine image, comprising:
   a clock configured to measure a time;
   a reference time receiver configured to receive a reference time used as a reference for a measuring of the time;
   a detection time memory configured to record detection times at each of which a radiation is detected, by using the time measured by the clock; and
   a revising circuit configured to revise the detection times recorded by the detection time memory, by using the reference time received by the reference time receiver,
   wherein the revising circuit revises the detection times by calculating a time error that occurred during an image taking period of a predetermined image taking process, by using a first time error and a second time error, and further distributing a calculated time error to each of the detection times recorded by the detection time memory during the image taking period,
   the first time error is a time error between the time measured by the clock and the reference time received by the reference time receiver at an image taking process starting time in an image taking, and
   the second time error is a time error between the time measured by the clock and the reference time received by the reference time receiver at an image taking process ending time in the image taking.

2. The nuclear medicine imaging apparatus according to claim 1, when the revising circuit comprises:
   a detection time error calculating circuit configured to calculate a time error between each of the detection times recorded by the detection time memory and the reference time received by the reference time receiver; and
   a time difference revising circuit configured to, by using time errors calculated by the detection time error calculating circuit as well as time errors between the reference time and test times recorded as times at each of which a radioactivity level is measured by a measuring apparatus configured to measure a radioactivity level of a pharmaceutical, revise time differences between the test times and the detection times.

3. The nuclear medicine imaging apparatus according to claim 1, further comprising:

a correcting circuit configured to correct the time measured by the clock, according to the reference time received by the reference time receiver; and wherein before performing a correction, the correcting circuit displays a checking screen on a display to check to see if a correction should be performed and judges whether a timing with which a correction is to be performed affects an image taking process, and, if a condition is satisfied where a permission to perform a correction has been received, but the correcting circuit judges a timing with which a correction is to be performed affects an image taking process, the correcting circuit cancels a correction.

4. The nuclear medicine imaging apparatus according to claim 3, wherein the correcting circuit performs a correction at a predetermined interval.

5. The nuclear medicine imaging apparatus according to claim 3, wherein before performing a correction, the correcting circuit judges whether timing with which a correction is to be performed affects an image taking process and, if the timing is such that the image taking process is to be affected, the correcting circuit cancels a correction.

6. The nuclear medicine imaging apparatus according to claim 3, wherein the correcting circuit performs a correction when the nuclear medicine imaging apparatus is activated.

7. A nuclear medicine imaging system including: a measuring apparatus configured to measure a radioactivity level of a nuclide with which a subject is dosed; and a nuclear medicine imaging apparatus configured to detect radiation emitted by the nuclide and to reconstruct a nuclear medicine image, wherein the measuring apparatus comprises:
a signal transmitter configured to transmit a signal indicating timing corresponding to a test time at which the radioactivity level is measured, to the nuclear medicine imaging apparatus, and the nuclear medicine imaging apparatus comprises:
a signal receiver configured to receive the signal transmitted by the signal transmitter;
a clock configured to measure a time while using the timing indicated by the signal received by the signal receiver as a starting point;
a reference time receiver configured to receive a reference time used as a reference for a measuring of the time;
a detection time recording memory configured to record detection times at which a radiation is detected, by using the time measured by the clock; and
a revising circuit configured to revise the detection times recorded by the detection time recording memory, by using the reference time received by the reference time receiver, wherein the revising circuit revises the detection times by calculating a time error that occurred during an image taking period of a predetermined image taking process, by using a first time error and a second time error, and further distributing a calculated time error to each of the detection times recorded by the detection time memory during the image taking period, the first time error is a time error between the time measured by the clock and the reference time received by the reference time receiver at an image taking process starting time in an image taking, and the second time error is a time error between the time measured by the clock and the reference time received by the reference time receiver at an image taking process ending time in the image taking.

* * * * *